US012333725B2

(12) United States Patent
Woicik et al.

(10) Patent No.: US 12,333,725 B2
(45) Date of Patent: Jun. 17, 2025

(54) SYSTEMS AND METHODS FOR DETERMINING TISSUE MICROARRAY SAMPLING PROTOCOLS

(71) Applicant: Insitro, Inc., South San Francisco, CA (US)

(72) Inventors: Adelaide Woicik, Bellevue, WA (US); Christopher Probert, Mill Valley, CA (US); Santiago Akle Serrano, San Francisco, CA (US); Zachary R. McCaw, Chapel Hill, NC (US); Benjamin Dulken, Menlo Park, CA (US); Sanjana Narayanan, Palo Alto, CA (US)

(73) Assignee: Insitro, Inc., South San Francisco, CA (US)

( * ) Notice: Subject to any disclaimer, the term of this patent is extended or adjusted under 35 U.S.C. 154(b) by 0 days.

(21) Appl. No.: 18/991,222

(22) Filed: Dec. 20, 2024

(65) Prior Publication Data

US 2025/0157030 A1    May 15, 2025

Related U.S. Application Data

(63) Continuation of application No. PCT/US2024/054979, filed on Nov. 7, 2024.
(Continued)

(51) Int. Cl.
*G06T 7/00* (2017.01)
*G06V 10/26* (2022.01)
(Continued)

(52) U.S. Cl.
CPC ............ *G06T 7/0012* (2013.01); *G06V 10/26* (2022.01); *G06V 10/764* (2022.01);
(Continued)

(58) Field of Classification Search
CPC .......... G01N 2035/00138; G01N 2035/00158; G01N 2291/02475; G16H 50/20;
(Continued)

(56) References Cited

U.S. PATENT DOCUMENTS

2002/0102011 A1\* 8/2002 Bacus .................... G16B 45/00
382/128
2012/0093387 A1\* 4/2012 Gholap .................. G06V 20/69
382/133

(Continued)

OTHER PUBLICATIONS

Guo et al., (2018). "Multi-region proteome analysis quantifies spatial heterogeneity of prostate tissue biomarkers," Life Sci Alliance, 1(2):e201800042, 15 pages.

(Continued)

*Primary Examiner* — Aaron W Carter
*Assistant Examiner* — Courtney Joan Nelson
(74) *Attorney, Agent, or Firm* — MORRISON & FOERSTER LLP

(57) ABSTRACT

An exemplary method for determining a sampling protocol for sampling tissue cores for a tissue microarray includes obtaining an initial plurality of tissue cores from an image of a tissue slide; selecting a first subset of the initial plurality of tissue cores based on a first candidate sampling protocol; inputting the first subset of the plurality of tissue cores into a machine learning model; evaluating the first candidate sampling protocol by evaluating a first output of the machine learning model; selecting a second subset of the initial plurality of tissue cores based on a second candidate sampling protocol; inputting the second subset of the plurality of tissue cores into the machine learning model; evaluating the second candidate sampling protocol by evaluating a second output of the machine learning model; and determining the sampling protocol based on the evaluation of the first
(Continued)

candidate sampling protocol and the second candidate sampling protocol.

29 Claims, 10 Drawing Sheets

Related U.S. Application Data

(60) Provisional application No. 63/548,140, filed on Nov. 10, 2023.

(51) Int. Cl.
*G06V 10/764* (2022.01)
*G06V 10/766* (2022.01)
*G06V 20/69* (2022.01)
*G16B 40/00* (2019.01)
*G16H 30/40* (2018.01)
*G16H 50/20* (2018.01)

(52) U.S. Cl.
CPC ........... *G06V 20/698* (2022.01); *G16B 40/00* (2019.02); *G16H 30/40* (2018.01); *G16H 50/20* (2018.01); *G06T 2207/10056* (2013.01); *G06T 2207/20081* (2013.01); *G06T 2207/30024* (2013.01); *G06T 2207/30096* (2013.01); *G06V 10/766* (2022.01); *G06V 2201/03* (2022.01)

(58) Field of Classification Search
CPC ........ G16H 50/30; G16B 50/00; G16B 40/00; G16B 30/20; G16B 40/30; G06T 2207/30024; G06T 7/0012; G06T 2207/10056; G06T 2207/30072; G06T 2207/20081; G06V 20/69
See application file for complete search history.

(56) References Cited

U.S. PATENT DOCUMENTS

2018/0247101 A1\* 8/2018 Wimberger-Friedl ...................... G06T 7/337
2019/0295721 A1 9/2019 Madabhushi et al.

OTHER PUBLICATIONS

Bockmayr et al., (2011). "Combinatorial Optimization and Integer Linear Programming Combinatorial Optimization: Introduction," Discrete Math for Bioinformatics WS 11/12, 2001-2022.
International Search Report and Written Opinion received for International Patent Application No. PCT/US2024/054979 mailed on Feb. 25, 2025, 19 pages.
Rubin et al., (2002). "Tissue microarray sampling strategy for prostate cancer biomarker analysis," American Journal Of Surgical Pathology, 26(3):312-319.

\* cited by examiner

SYSTEMS AND METHODS FOR DETERMINING TISSUE MICROARRAY SAMPLING PROTOCOLS

CROSS REFERENCE TO RELATED APPLICATIONS

This application is a continuation application of International Application No. PCT/US2024/054979, filed internationally on Nov. 7, 2024, which claims the priority benefit of U.S. Provisional Patent Application Ser. No. 63/548,140, filed Nov. 10, 2023, the disclosures of which are herein incorporated by reference in their entirety.

FIELD

This disclosure relates generally to medical image processing and more specifically to in silico selection of tissue microarray samples for machine learning (ML) tasks.

BACKGROUND

Tissue section acquisition and imaging is a common step in cancer clinical care. Recently, ML approaches have been developed to diagnose and predict important clinical endpoints from histopathology images, including patient survival, genetic mutations, cancer subtype, and properties of the tumor microenvironment. Digitized histology slides, known as Whole Slide Images (WSIs), typically contain a single macroscopic Whole Tissue Section (WTS). While WTS slides provide abundant microenvironmental context for image analysis, they can be cost prohibitive for multiplexed assays.

As an alternative to WTSs, tissue microarrays (TMAs) are small cylindrical sections of tissue called cores that are extracted from a larger tissue block with a needle, sectioned, and placed into a well plate for subsequent analysis. A stain is applied to each experimental slide, such that the cost of staining scales with the number of slides rather than the number of patients. While a single slide typically contains only one WTS, TMA cores from over 200 patients can be stored on the same slide and stained simultaneously, thereby amortizing the cost of experimental staining over multiple patients. While different approaches for selecting tissue to be included in a TMA exist, the impact of the sampling procedure on downstream machine learning-model performance is underexplored. Additionally, there is no standard method for generating TMAs, and existing studies vary in their core sampling protocols. Thus, what is needed is a standard, generalizable approach for determining optimal TMA core sampling protocols for various ML models and tasks.

SUMMARY

Described herein are systems, methods, devices, apparatuses, and non-transitory computer readable storage media directed to determining TMA core sampling protocols suited for different machine learning models and/or tasks. An exemplary system may identify a plurality of tissue cores that can be obtained from an image of a tissue sample. The system may then select one or more subsets of that plurality according to different candidate sampling protocols and input the selected subsets into a machine learning model. Finally, the system may evaluate each candidate sampling protocol based on the respective outputs of the machine learning model to determine the best sampling protocol for a given machine learning model and/or task. The outputs may be evaluated by comparing each output to a ground truth value, to outputs obtained based on the other subsets, or to an output obtained by inputting the whole slide image of a whole tissue section (e.g., an embedding generated based on the whole slide image) into the machine learning model.

The techniques described herein provide a number of technical advantages. For example, in silico simulation of TMA cores from whole slide images (WSIs) provides a comparatively inexpensive and efficient way to refine core selection procedures. It also expands the sampling approaches that can be tested by providing different selection criteria to the pipeline. Further, the ability to optimize TMA design (e.g., core size, number of cores per patient) enables more rapid and efficient acquisition of data (e.g., stained tissue specimens) for downstream machine learning tasks. In silico TMAs can be fed to downstream machine learning tasks to test the tradeoffs of different core sampling strategies with respect to cost and model performance. The systems and methods described herein provide a structured and standardized method for generating TMAs suitable for different machine learning models and/or machine learning tasks. By standardizing the core selection approach, the systems and methods described herein may improve the functioning of a computer by increasing computer processing speed, reducing processing and power requirements, and reducing memory requirements. For instance, by providing a standardized method for determining an optimal selection protocol for TMA core datasets, less processing time, power, and speed may be required to determine optimal sampling protocols for different tasks, as the same method may be applied to determine the best sampling protocol for a variety of downstream tasks. Additionally, by utilizing TMA cores, less data storage may be required as compared to WSIs.

In some aspects, provided herein is a method for determining a sampling protocol for sampling tissue cores for a tissue microarray, the method comprising: obtaining an initial plurality of tissue cores from an image of a tissue slide; selecting a first subset of the initial plurality of tissue cores based on a first candidate sampling protocol; inputting the first subset of the plurality of tissue cores into a machine learning model; evaluating the first candidate sampling protocol by evaluating a first output of the machine learning model based on the first subset of the plurality of tissue cores; selecting a second subset of the initial plurality of tissue cores based on a second candidate sampling protocol; inputting the second subset of the plurality of tissue cores into the machine learning model; evaluating the second candidate sampling protocol by evaluating a second output of the machine learning model based on the second subset of the plurality of tissue cores; and determining the sampling protocol based on the evaluation of the first candidate sampling protocol and the second candidate sampling protocol.

In some embodiments, the method further comprises selecting a third subset of the initial plurality of tissue cores based on a third candidate sampling protocol; inputting the third subset of the plurality of tissue cores into the machine learning model; evaluating the third candidate sampling protocol by evaluating a third output of the machine learning model based on the third subset of the plurality of tissue cores; and wherein the determination of the sampling protocol is further based on the evaluation of the third candidate sampling protocol.

In some embodiments, the first output, the second output, and the third output comprise a disease diagnosis, a probability of survival, a disease subtype, a genetic sequence, a rare variant association, or any combination thereof.

In some embodiments, the first output of the machine learning model comprises: comparing the first output of the machine learning model to a ground truth value; and wherein evaluating the second output of the machine learning model comprises comparing the second output to at least one of the ground truth value and the first output.

In some embodiments, the first candidate sampling protocol specifies any one or more of: a first number of the tissue cores in the first subset, a first tissue core size, a first amount of tissue in each core of the first subset, a first minimum distance between each tissue core of the first subset and an edge of a tissue, and one or more first tissue labels corresponding to one or more regions of the tissue slide.

In some embodiments, generating the second candidate sampling protocol comprises any of: modifying the first number of the tissue cores, modifying the first tissue core size, modifying the first amount of tissue in each core, modifying the first minimum distance between each tissue core of the first subset and the edge of the tissue edge, and modifying the one or more first tissue labels.

In some embodiments, the one or more first tissue labels corresponding to the one or more regions of the tissue slide are associated with a diseased tissue or a healthy tissue.

In some embodiments, the one or more first tissue labels corresponding to the one or more regions of the tissue slide are associated with any of: an invasive carcinoma; a carcinoma in situ, a tumor invasive front, necrotic tissue, or a healthy tissue.

In some embodiments, the one or more first tissue labels are based on one or more tissue labels assigned to the or more regions of the image by providing the image to an image segmentation model.

In some embodiments, the image segmentation model is trained based on labeled tissue slide images.

In some embodiments, a respective tissue label of the one or more first tissue labels is assigned to a pixel of the image.

In some embodiments, the initial plurality of tissue cores is obtained using integer linear programming by maximizing an objective function based on a set of constraint parameters.

In some embodiments, the set of constraint parameters comprises a tissue core size, a minimum distance between two tissue cores, a minimum tissue content, a minimum distance between a tissue core and an edge of a tissue edge, or any combination thereof.

In some embodiments, the initial plurality of tissue cores comprises a number of tissue cores that can be obtained from the tissue slide based on the set of constraint parameters.

In some embodiments, the machine learning model comprises a trained classifier model or a trained regression model.

In some embodiments, the tissue slide comprises any of: cancerous tissue, tumor-adjacent normal tissue, necrotic tissue, and randomly sampled tissue.

In some embodiments, inputting the first subset into the machine learning model comprises: generating at least one embedding based on each tissue core of the first subset of the initial plurality of tissue cores; and inputting the at least one embedding into the machine learning model.

In some aspects, provided herein is a system for determining a sampling protocol for sampling tissue cores for a tissue microarray, the system comprising one or more processors, memory, and one or more programs stored in the memory for execution by the one or more processors, the one or more programs including instructions that when executed by the one or more processors cause the system to: obtain an initial plurality of tissue cores from an image of a tissue slide; select a first subset of the initial plurality of tissue cores based on a first candidate sampling protocol; input the first subset of the plurality of tissue cores into a machine learning model; evaluate the first candidate sampling protocol by evaluating a first output of the machine learning model based on the first subset of the plurality of tissue cores; select a second subset of the initial plurality of tissue cores based on a second candidate sampling protocol; input the second subset of the plurality of tissue cores into the machine learning model; evaluate the second candidate sampling protocol by evaluating a second output of the machine learning model based on the second subset of the plurality of tissue cores; and determine the sampling protocol based on the evaluation of the first candidate sampling protocol and the second candidate sampling protocol.

In some aspects, provided herein is a non-transitory computer-readable medium storing instructions for determining a sampling protocol for sampling tissue cores for a tissue microarray, wherein the instructions are executable by a system comprising one or more processors to cause the system to: obtain an initial plurality of tissue cores from an image of a tissue slide; select a first subset of the initial plurality of tissue cores based on a first candidate sampling protocol; input the first subset of the plurality of tissue cores into a machine learning model; evaluate the first candidate sampling protocol by evaluating a first output of the machine learning model based on the first subset of the plurality of tissue cores; select a second subset of the initial plurality of tissue cores based on a second candidate sampling protocol; input the second subset of the plurality of tissue cores into the machine learning model; evaluate the second candidate sampling protocol by evaluating a second output of the machine learning model based on the second subset of the plurality of tissue cores; and determine the sampling protocol based on the evaluation of the first candidate sampling protocol and the second candidate sampling protocol.

BRIEF DESCRIPTION OF THE FIGURES

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
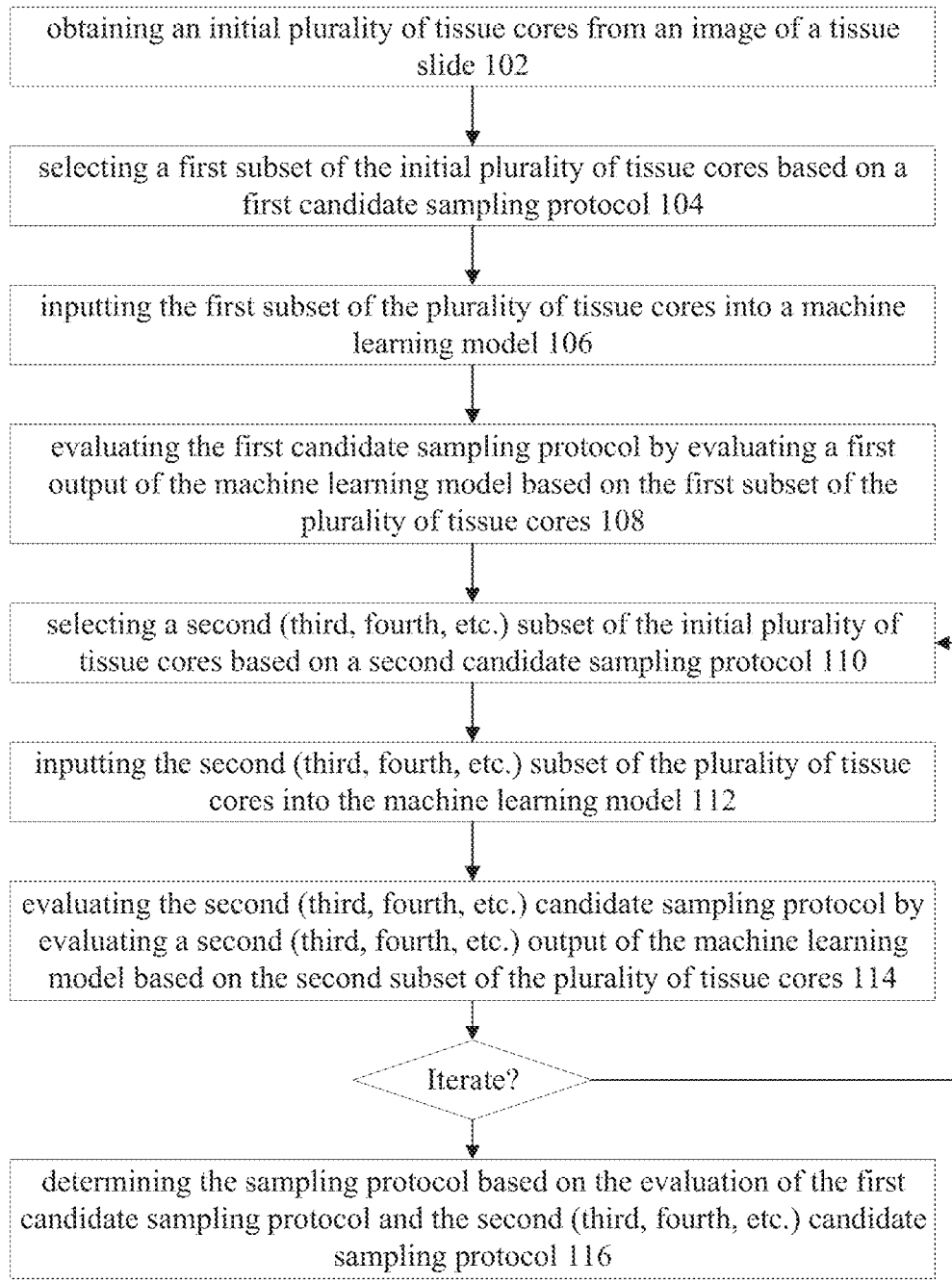
FIG. 1 illustrates an exemplary method for determining a sampling protocol for tissue cores according to some embodiments.

Described herein are systems, methods, devices, apparatuses, and non-transitory computer readable storage media directed generally to determining in silico tissue microarray (TMA) core (i.e., in silico tissue microarray cores) sampling protocols suited for different machine learning models and/or tasks. The systems and methods described herein may be divided into three main components: initial core placement, core subset sampling, and core evaluation. Core placement may include identifying a maximum number of cores that can be obtained from an image of a tissue slide based on a set of constraints. For instance, an exemplary system may obtain (e.g., determine) an initial plurality of cores from an image of a tissue slide. The image may be a WSI of a tissue sample, and the initial plurality may be determined using an integer linear programming method, in which the system determines a maximum number of cores that can be obtained from the WSI based on a set of constraints. The set of constraints may include, for instance, core size, tissue content, or other constraints as described further throughout, and the system may determine that the maximal core placement has been achieved when no additional cores can be obtained from the image without violating one or more of the constraints.

Once the initial plurality of cores have been obtained for a WSI, the exemplary system may obtain one or more subsets of cores from the initial plurality based on one or more candidate sampling protocols. The subset(s) may be used to form at least one tissue microarray (TMA) core data set for downstream machine learning model evaluation. A candidate sampling protocol may specify one or more parameters that define which cores should be selected from the initial plurality to include in the subset. For instance, a candidate sampling protocol may specify core size, a number of cores to be included in the subset, labels corresponding to one or more regions of the tissue sample from which the cores should be selected, and/or other parameters described further throughout. The tissue label(s) specified in the candidate sampling protocol may be based on one or more tissue labels assigned to one or more regions of a whole slide image by an image segmentation (e.g., classification) model, and may include labels such as "invasive carcinoma," "healthy tissue," "necrotic tissue," and so on as described throughout.

In some embodiments, after selecting a first subset of cores from the initial plurality, the system may input the first subset of cores into a machine learning model. The machine learning model may provide an output such as a disease diagnosis, a probability of survival, a disease subtype, a genetic sequence, a rare variant association, or any combination thereof, and the system may evaluate the output by, for instance, comparing the output to a ground truth value and/or comparing the output to an output obtained by inputting a WSI into the machine learning model. In some embodiments, inputting the first subset of cores (and/or WSI) into the machine learning model includes generating at least one embedding based on each tissue core of the first subset of the initial plurality of tissue cores (and/or at least one embedding based on the WSI); and inputting the at least one embedding into the machine learning model. In such embodiments, the output may be generated based on the embedding(s).

In some embodiments, after selecting a first subset of cores (or in parallel to), inputting the first subset of cores into a machine learning model, and evaluating the output, the system may select a second subset of cores based on a second candidate sampling protocol. The second candidate sampling protocol may specify one or more different parameters (e.g., core size, number of cores, tissue label, etc.) from the first candidate sampling protocol. The second subset may then be input into the machine learning model (e.g., after generating embedding(s) based on each core of the subset) and an output of the model may be evaluated (e.g., by comparing the output to a ground truth value, the first output generated based on the first subset of cores, or an output obtained based on the WSI) to determine whether the first or second candidate sampling protocol is better suited for the respective machine learning model and/or machine learning task. Based on the evaluation of each output, the system may determine that the better performing candidate sampling protocol should be utilized when obtaining TMA cores for the respective machine learning model/task. In some embodiments, the system may iteratively select any number of additional subsets (e.g., 1, 2, 3, ... N) based on additional candidate sampling protocols and repeat the evaluation process described above.

While the process described above refers to two subsets selected from a single whole slide image based on two candidate sampling protocols, it should be understood that the process may be applied across any number of whole slide images for any number of subsets and any number of candidate sampling protocols. For instance, in an exemplary study described below, 16 synthetic TMA breast carcinoma datasets are evaluated for predicting patient overall survival, immunohistochemistry subtype, and mutation status. Several common design principles were deduced that are broadly applicable across TMA applications.

As described above, the techniques described herein provide a number of technical advantages. For example, in silico simulation of TMA cores from whole slide images (WSIs) provides a comparatively inexpensive and efficient way to refine core selection procedures. It also expands the sampling approaches that can be tested by providing different selection criteria to the pipeline. In silico TMAs can be fed to downstream machine learning tasks to test the tradeoffs of different core sampling strategies with respect to cost and model performance. The systems and methods described herein provide a structured and standardized method for generating TMAs suitable for different machine learning models and/or machine learning tasks. By standardizing the core selection approach, the systems and methods described herein may improve the functioning of a computer by increasing computer processing speed, reducing processing and power requirements, and reducing memory requirements. For instance, by providing a standardized method for determining an optimal selection protocol for TMA core datasets, less processing time, power, and speed may be required to determine optimal sampling protocols for different tasks, as the same method may be applied to determine the best sampling protocol for a variety of downstream tasks. Additionally, by utilizing TMA cores, less data storage may be required as compared to WSIs.

In the following description of the various embodiments, it is to be understood that the singular forms "a," "an," and "the" used in the following description are intended to include the plural forms as well, unless the context clearly indicates otherwise. It is also to be understood that the term "and/of" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The structure for a variety of these systems will appear from the description below. In addition, the present invention is not described with reference to any particular programming language. It will be appreciated that a variety of programming languages may be used to implement the teachings of the present disclosure as described herein.

FIG. 1 illustrates an exemplary process 100 for determining a sampling protocol for sampling tissue cores for a tissue microarray, according to some embodiments. Process 100 is performed, for example, using one or more electronic devices implementing a software platform. In some examples, process 100 is performed using one or more electronic devices. In some embodiments, process 100 is performed using a client-server system, and the blocks of process 100 are divided up in any manner between the server and one or more client devices. Thus, while portions of process 100 are described herein as being performed by particular devices, it will be appreciated that process 100 is not so limited. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

At block 102, an exemplary system (e.g., one or more electronic devices) obtains an initial plurality of tissue cores based on a first candidate sampling protocol. The tissue cores may be obtained from a whole slide image of a tissue sample. A whole slide image may refer to a digital file resulting from a scan of a complete microscope slide of a tissue sample (e.g., a stained or unstained tissue sample), and the tissue sample may include, for instance, cancerous tissue, tumor-adjacent normal tissue, necrotic tissue, and/or randomly sampled tissue. While process 100 is described with reference to a single whole slide image and two candidate sampling protocols, it should be understood that datasets of tissue cores may be obtained from any number of whole slide images using any number of candidate sampling protocols, and that the sampling protocols may be evaluated using any number of different machine learning models/ machine learning tasks. A tissue core may include a small segment of tissue within the whole slide image, and a tissue microarray may be an array of such cores. The initial plurality may be positioned (e.g., overlaid) by the system on the whole slide image of the tissue sample based on a set of constraint parameters.

In some embodiments, the initial plurality of tissue cores is obtained using integer linear programming, for instance, as described in detail with reference to FIG. 2A and an exemplary study conducted using a publicly available dataset of whole slide images presented below, which may enable the exemplary system to obtain the maximum number of cores from a whole slide image given various constraint parameters. In other words, the system obtains the initial plurality of tissue cores by maximizing an objective function based on a set of constraint parameters. The set of constraint parameters may include, for instance, a tissue core size (e.g., diameter), a minimum distance between two tissue cores, a minimum tissue content (i.e., approximately how much tissue each core should contain, measured, for instance, by area), a minimum distance between a tissue core and an edge of the tissue, or any combination thereof. Accordingly, the constraint parameters may impact the number of tissue cores that can be obtained from the tissue slide. For example, if the constraint parameters define a tissue core size of 1.5 mm, the initial plurality of tissue cores will include fewer tissue cores than if the constraint parameters define a tissue core size of 0.5 mm.

At block 104, the exemplary system selects a first subset of the initial plurality of tissue cores based on a first candidate sampling protocol. The first candidate sampling protocol may specify any one or more of: a first number of the tissue cores in the first subset, a first tissue core size, one or more first tissue labels corresponding to one or more regions of the tissue slide, a distance between a selected core and another core in the initial plurality, an amount of tissue contained in a core, a distance between a core from an edge of a tissue block, etc. The candidate sampling protocol may be determined automatically by the system (e.g., a core size, number of cores, etc. may be randomly selected by the system), and/or a user may input various parameters of the candidate sampling protocol.

The one or more first tissue labels corresponding to the one or more regions of the tissue slide may be associated with any characteristic of a tissue to be studied (e.g., a disease, symptom of a disease, morphological trait, a characteristic of a healthy tissue, cellular structures or substructures, and so on). The one or more first tissue labels corresponding to the one or more regions of the tissue slide may be associated with diseased tissue or healthy tissue. For instance, the one or more first tissue labels corresponding to the one or more regions of the tissue slide may be associated with, for instance, any of: an invasive carcinoma, a carcinoma in situ, a tumor invasive front, necrotic tissue, lobular carcinoma in situ, ductal carcinoma in situ, a healthy tissue, etc. The one or more first tissue labels of the candidate sampling protocol may be based on one or more tissue labels assigned to the one or more regions of the image by providing the image to an image segmentation model. For instance, the image segmentation model may assign labels to regions of the image (e.g., to each pixel of the image, or groups of pixels in the image), and the candidate sampling protocol may specify labels that should be included in (or excluded from) the subset.

The image segmentation model may be trained based on labeled tissue slide images. In some embodiments, the image segmentation model is a classifier model. The one or more tissue labels assigned to the or more regions of the image by providing the image to an image segmentation model may be assigned prior to selecting the first subset. In some embodiments, the one or more tissue labels assigned to the or more regions of the image by providing the image to an image segmentation model may be assigned in parallel with obtaining the initial plurality of tissue cores based on a first candidate sampling protocol. For instance, the whole slide image may be simultaneously processed using linear integer programming to obtain the initial plurality of tissue cores and using a classifier model to assign labels to regions of the whole slide image. Tissue labels may be assigned to each pixel and/or groups of pixels of the image using the image segmentation model.

At block 106, the system inputs the first subset of the plurality of tissue cores into a machine learning model. The machine learning model may include a trained classifier model or a trained regression model, and may be configured to provide, for instance, a disease diagnosis, a probability of survival, a disease subtype, a genetic sequence, a rare variant association, or any combination thereof. The machine learning model may be trained using labeled images of biological tissue samples, for instance, labeled images of tissue microarray cores. In some embodiments, the machine learning model may be trained using unlabeled images that do not depict biological tissue samples and retrained using labeled images that depict biological tissue samples.

Inputting the first subset of the plurality of tissue cores into the machine learning model may include generating at least one embedding based on each tissue core of the first subset of the initial plurality of tissue cores and inputting at least one embedding into the machine learning model. An embedding is a vector representation of a tissue core. An embedding may represent various morphological or positional characteristics of cells and/or cellular structures/substructures in a tissue sample. Each embedding may capture rich semantic information about the imaging data (e.g., features of the microscopic structure of tissues reflected in the image, which may include cellular substructures), while excluding information that is not relevant to downstream analyses (e.g., orientation of the image). The number of embeddings generated for each tissue core may vary based on the size of the core. For instance, at least one embedding may be generated for each tissue core of a given subset of tissue cores; however, more than one (e.g., 10, 50, 100, 1000, or more) may be generated for each embedding. It should be understood that any number of embeddings may be generated for each tissue core.

Figure 3:
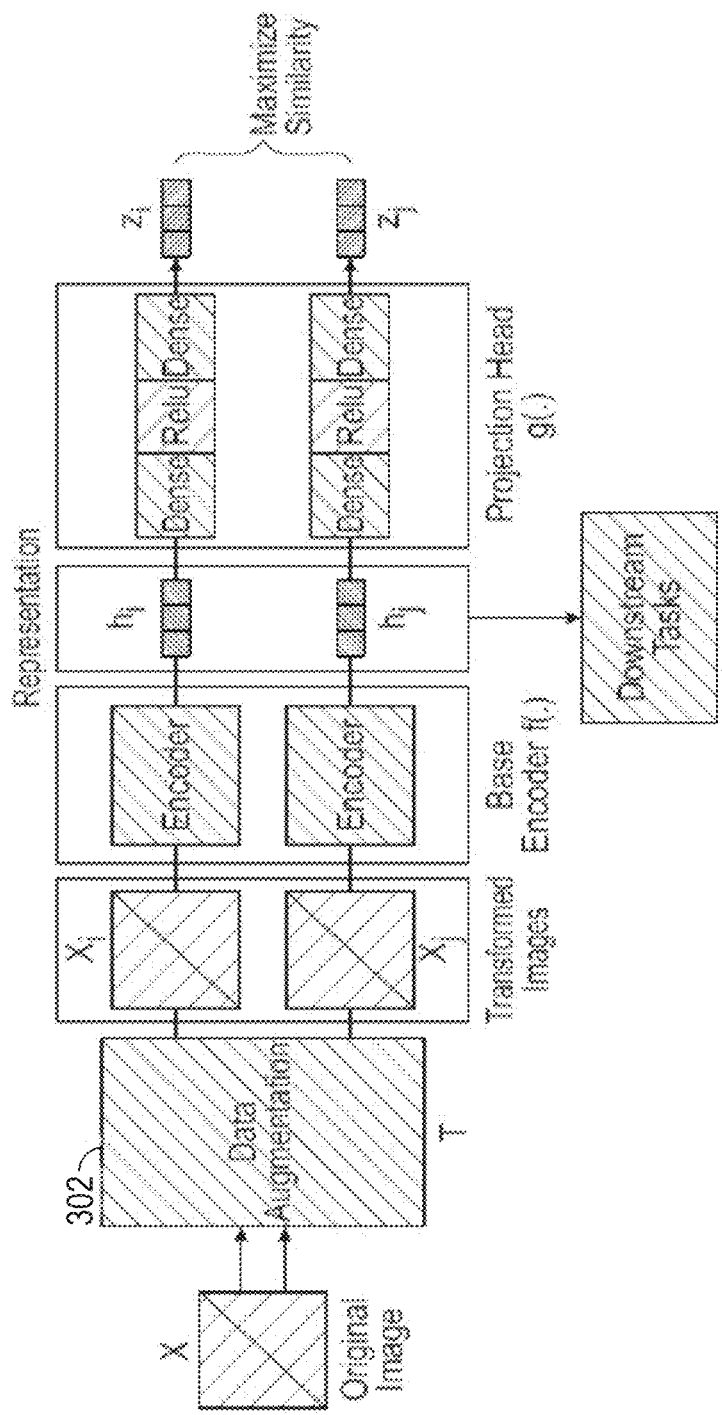
FIG. 3 illustrates an exemplary contrastive learning method according to some embodiments.

The embedding may be generated by inputting the tissue core images into a trained embedding model. The embedding model may be a self-supervised or unsupervised model, such as a Hierarchical Image Pyramid Transformer (HIPT) model or SimCLR (Simple Framework for Contrastive Learning of Visual Representations) model. FIG. 3, described below, illustrates a training process for an exemplary contrastive learning algorithm, such as SimCLR, that may be used to generate embeddings based on the subsets of tissue microarray cores described herein.

At block 108, the system (or a user of the system) evaluates the first candidate sampling protocol by evaluating a first output of the machine learning model based on the first subset of the plurality of tissue core. Evaluating the first output of the machine learning model may include comparing the first output of the machine learning model to a ground truth value. For instance, a disease diagnosis output may be compared to a known disease of the tissue core. Evaluating the first output of the machine learning model may include comparing the first output of the machine learning model to an output generated by inputting at least one embedding generated based on the whole slide image into the machine learning model. For example, one or more embeddings may be generated using the subset of tissue microarray core images as described above, and one or more embeddings may be generated based on the WSI from which the subset was obtained. The embeddings generated based on the subset of tissue microarray core images may be input into the machine learning model to generate an output, and the embeddings generated based on the WSI may be input into the machine learning model to generate an output. The two outputs may be compared to determine the model's performance using the tissue microarray core embedding inputs relative to the whole slide image embedding input.

Outputs generated by classification and regression models may be evaluated based on one or more metrics. For instance, a classification output may be evaluated using metrics such as accuracy, precision, sensitivity, area under the receiver operating characteristic (AUC-ROC), and so on. A regression output may be evaluated using metrics such as mean absolute error, mean squared error, root mean squared error, an R-squared value, and so on.

At block 110, the system may select a second subset of the initial plurality of tissue cores based on a second candidate sampling protocol. The second subset may subsequently be input into the same machine learning model in order to compare the model's performance relative to its performance based on the first subset, as described further below. This may provide an indication of which candidate sampling protocols are better suited for a given machine learning model and/or machine learning task. The second subset may not include any cores included in the first subset (i.e., there may be no overlap between the cores of the first and second subset). The second subset may include one or more cores included in the first subset and one or more cores not included in the first subset (i.e., the first and second subset may at least partially overlap).

The second candidate sampling protocol may be generated by modifying one or more parameters of the first candidate sampling protocol. Generating the second candidate sampling protocol may include any of: modifying the first number of the tissue cores, modifying the first tissue core size, and modifying the one or more first tissue labels, modifying a distance between a selected core and another core in the initial plurality, modifying an amount of tissue contained in a core, modifying a distance between a core from an edge of a tissue block, or any combination thereof. For instance, the first candidate sampling protocol may specify 10 tissue cores, each of size 1.0 mm, taken from a region of tissue assigned an invasive carcinoma tissue label. Meanwhile, the second candidate sampling protocol may specify 10 tissue cores, each of size 1.2 mm, taken from a region of tissue assigned a carcinoma in situ label. It should be understood that any of the parameters (e.g., size, number of cores, or tissue label) may be modified from the first candidate sampling protocol to generate the second candidate sampling protocol. Accordingly, the second candidate sampling protocol may specify one or more different parameters (e.g., core size, tissue content, tissue label, etc. from the first candidate sampling protocol).

In some embodiments, a second subset may be selected from an initial plurality of cores obtained based on a different whole slide image than the first subset was selected from. For example, an initial plurality of cores may be obtained from any number of whole slide images using an integer linear programming approach applied to each of the whole slide images (i.e., a maximum number of cores may be obtained for each individual whole slide image). Subsets of cores may then be selected from the initial (maximal) plurality of cores obtained for each of the respective whole slide images and input into downstream machine learning models. In some embodiments, one or more different candidate sampling protocols may be applied to different whole slide images (e.g., different size cores may be obtained from each whole slide image, a subset of differently labeled cores may be obtained from each whole slide image, etc.). In some embodiments, a set of candidate sampling protocols (e.g., 2, 5, 10, 20, 50, 100, greater than 100, or any number therebetween) may be defined and applied to a dataset of whole slide images. In some embodiments, one or more sampling protocols may be applied to each whole slide image in the data set to select a subset of cores from an initial (maximal) plurality of cores obtained for the whole slide image.

In some embodiments, any number (including all) of the candidate sampling protocols may be applied to each whole slide image in the data set to select multiple subsets of cores from the initial (maximal) plurality of cores obtained for each of the whole slide images. For example, if a dataset includes 100 whole slide images, and a set of 10 different candidate sampling protocols is defined, then 10 different subsets of cores may be obtained from each of the 100 whole slide images corresponding to each of the candidate sampling protocols. In some embodiments, the 100 whole slide images may correspond to 100 different patients. Thus, in such an example, a data set of tissue microarray cores may be constructed for each candidate sampling protocol that includes a subset of tissue microarray core images from each of the 100 patients. These datasets of tissue microarray core images may then be input into downstream machine learning tasks to evaluate the performance of the models and thus identify the best performing sampling protocol. It should be understood that the numbers of whole slide images and candidate sampling protocols described above are meant to be exemplary and not limiting. The systems and methods described herein may include any number of candidate sampling protocols applied to any number of whole slide images.

At block 112, the system may input the second subset of tissue cores into the machine learning model. Configurations, weighting, etc. of the machine learning model may be updated based on the evaluation of the first candidate sampling protocol prior to inputting the second subset into the machine learning model, or the configurations, weighting, etc. may be retained between each subset to better isolate the impact of the candidate sampling protocols on the machine learning model's performance.

At block 114, the system (or a user of the system) evaluates the second candidate sampling protocol by evaluating a second output of the machine learning model based on the second subset of the plurality of tissue cores. The second output may include a disease diagnosis, a probability of survival, a disease subtype, a genetic sequence, a rare variant association, or any combination thereof. The second output may include the same type of output as the first output. For instance, if the first output based on the first subset of tissue cores is a disease diagnosis, then the second output may also be a disease diagnosis (e.g., such that the model's ability to accurately predict a disease diagnosis based on the first and second candidate sampling protocols can be evaluated).

The evaluation of the second candidate sampling protocol may include any of the evaluation methods described above with reference to evaluation of the first candidate sampling protocol at block 108. Accordingly, a classification output may be evaluated using metrics such as accuracy, precision, sensitivity, area under the receiver operating characteristic (AUC-ROC), and so on. A regression output may be evaluated using metrics such as mean absolute error, mean squared error, root mean squared error, an R-squared value, and so on. Evaluating the second output of the machine learning model may include comparing the second output to at least one of the ground truth value and/or the first output and/or an output generated by inputting the whole slide image (e.g., an embedding generated based on the whole slide image) into the machine learning model. In some embodiments, the second output may be compared to the ground truth value to determine a performance metric, and the performance metric determined based on the second output may be compared to a performance metric determined based on the first output to determine a relative performance of the model using the first and second subsets. Accordingly, the comparison may be made between metrics such as an accuracy, precision, sensitivity, area under the receiver operating characteristic (AUC-ROC), and so on, of the first and second outputs.

In some embodiments, after evaluating the second candidate sampling protocol at block 114, the exemplary system (or a user of the system) may determine whether to iterate the process by selecting an additional subset and evaluating a candidate sampling protocol used to obtain the additional subset. For instance, the exemplary system may select a third (fourth, fifth, . . . Nth) subset of the initial plurality of tissue cores based on a third (fourth, fifth, . . . Nth) candidate sampling protocol. The system may then input the third (fourth, fifth, . . . Nth) subset of the plurality of tissue cores into the machine learning model and evaluate the third (fourth, fifth, . . . Nth) candidate sampling protocol by evaluating a third (fourth, fifth, . . . Nth) output of the machine learning model based on the third (fourth, fifth, . . . Nth) subset of the plurality of tissue cores. The system may iterate the core selection and evaluation process for any number of candidate sampling protocols.

The third (fourth, fifth, . . . Nth) candidate sampling protocol may be generated by modifying one or more parameters of the first and/or second candidate sampling protocol(s) (i.e., the third (or fourth, fifth, . . . Nth) candidate sampling protocol may include one or more different parameters from the first and/or second candidate sampling protocols, and/or any other candidate sampling protocol). Generating the third (fourth, fifth, . . . Nth) candidate sampling protocol may include any of: modifying a number of the tissue cores (e.g., modifying the first, second . . . Nth number of tissue cores), modifying a tissue core size (e.g., modifying the first, second . . . Nth tissue core size), modifying the one or more tissue labels (e.g., modifying the first, second . . . Nth tissue labels), modifying a distance between a selected core and another core in the initial plurality, modifying an amount of tissue contained in a core, modifying a distance between a core from an edge of a tissue block, or any combination thereof. For instance, the first candidate sampling protocol may specify 10 tissue cores, each of size 1.0 mm, taken from a region of tissue assigned an invasive carcinoma tissue label. Meanwhile, the third candidate sampling protocol may specify 15 tissue cores, each of size 1.5 mm, taken from a region of tissue assigned a carcinoma in situ label. It should be understood that any of the parameters (size, number of cores, or tissue label) may be modified from the first candidate sampling protocol to generate the second candidate sampling protocol. In some embodiments, each subset may be selected from a region of tissue assigned the same label (e.g., each subset may be selected from a region labeled invasive carcinoma), and the candidate sampling protocol may be evaluated based on a machine learning model's ability to accurately predict the correct label (e.g., disease diagnosis) to determine, for instance, an optimal core size or an optimal amount of tissue in a core for a machine learning model configured to predict a respective disease diagnosis.

At block 116, the system determines the sampling protocol based on the evaluation of the first candidate sampling protocol and the second candidate sampling protocol. The system may select the candidate sampling protocol that resulted in the best performance of the machine learning model as determined by the evaluation of the machine learning model's output. The best candidate sampling protocol may result in an output that is most similar to a ground truth value, and/or most similar to an output obtained based on the whole slide image (e.g., based on an embedding generated using the whole slide image). For example, if the machine learning model produced a more accurate, precise, etc. output based on the second subset than based on the first subset, this may indicate that the second candidate sampling protocol is better suited for that machine learning model and/or machine learning task than the first candidate sampling protocol. After determining the sampling protocol, that sampling protocol may be applied whenever using the machine learning model and/or for the machine learning task that was evaluated based on the first and second outputs.

Figure 2A:
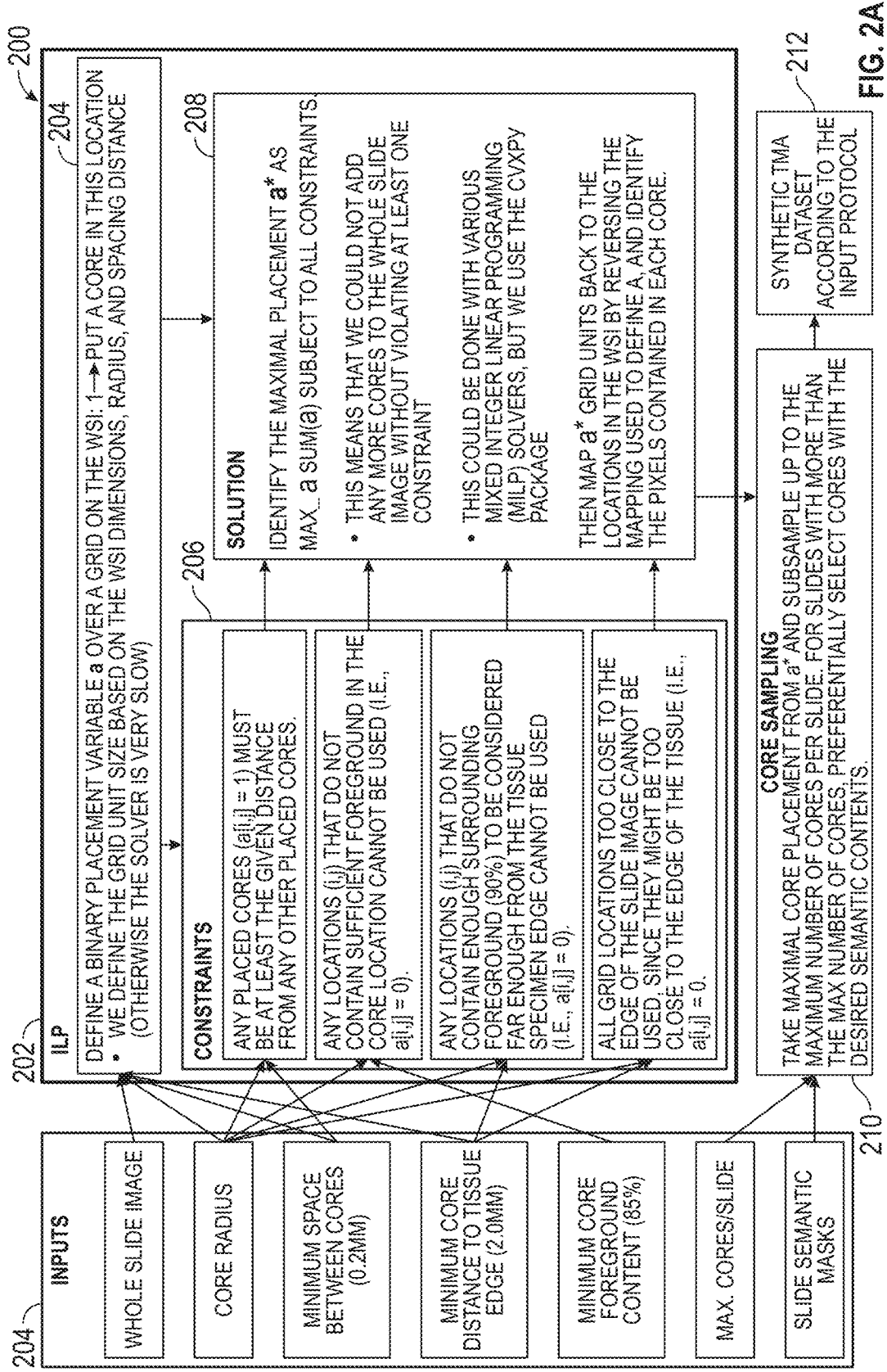
FIG. 2A illustrates detailed steps of an exemplary process for obtaining a maximum number of tissue cores from a whole slide image according to some embodiments.

FIG. 2A illustrates an exemplary integer linear programming process 202 for obtaining an initial plurality of cores and an exemplary subset selection step 210 which may be performed as part of the process 100 to obtain the initial plurality of cores and select subsets of cores from the initial plurality as described above with reference to FIG. 1.

As shown, an exemplary integer linear programming process 202 that may be utilized to select an initial plurality of cores includes defining a binary placement variable a over a grid (where if a=1, that means a core should be placed on that location of the grid) on a whole slide image (WSI) based on a set of input parameters, and then solving for the maximal placement for a* (the maximum sum of a, or the placement of variables a over the grid which results in the largest sum due to the highest number of is placed on the grid) based on a set of constraints, as set forth in further detail below.

At block 204, an exemplary system defines a binary placement variable a over a grid on the whole slide image (WSI) (e.g., 1=place a core in this location on the grid). A grid unit size may be defined based on one or more of inputs 204. For instance, the grid unit size may be defined based on the dimensions of the WSI, a radius of the tissue cores, a minimum distance between each core, and a minimum distance between each core and an edge of the tissue.

At block 206, an exemplary system defines a set of constraints, which constrain the solution for the maximal placement of cores a* described above. The constraints may be based on one or more of inputs 204. For instance, the constraints may include any one or more of the following: any placed cores (a[i, j]=1) must be at least a minimum distance from any of the other placed cores, any locations (i, j) that do not contain sufficient foreground in the core location cannot be used (i.e., a[i, j]=0), any locations (i, j) that do not contain enough surrounding foreground (90%) to be considered far enough from the tissue specimen edge cannot be used (i.e., a[i, j]=0), and/or all grid locations too close to the edge of the slide image cannot be used, since they might be too close to the edge of the tissue (i.e., a[i, j]=0).

At block 208, the system may solve for the maximal placement a* (e.g., as max_a sum(a)) subject to all constraints established at block 206. A solution is reached when no additional cores can be obtained from the WSI without violating at least one of the constraints. The maximal placement a* can be solved for using various mixed integer linear programming (mILP) solvers (e.g., the cvxpy package). The system may then map a* grid units back to the locations in the WSI by reversing the mapping used to define a, and identify the pixels contained in each core of the initial plurality of cores.

At block 210, the exemplary system may take the maximal core placement from a* and select subsets of up to the maximum number of cores per slide. For slides with more than the requisite number of cores, the system may preferentially select cores corresponding to tissue assigned a desired tissue label (e.g., carcinoma, etc.). The selected subsets may be used to create one or more synthetic tissue microarray core datasets for downstream machine learning tasks, as described above with reference to FIG. 1, and below with reference to an exemplary core selection study.

Figure 2B:
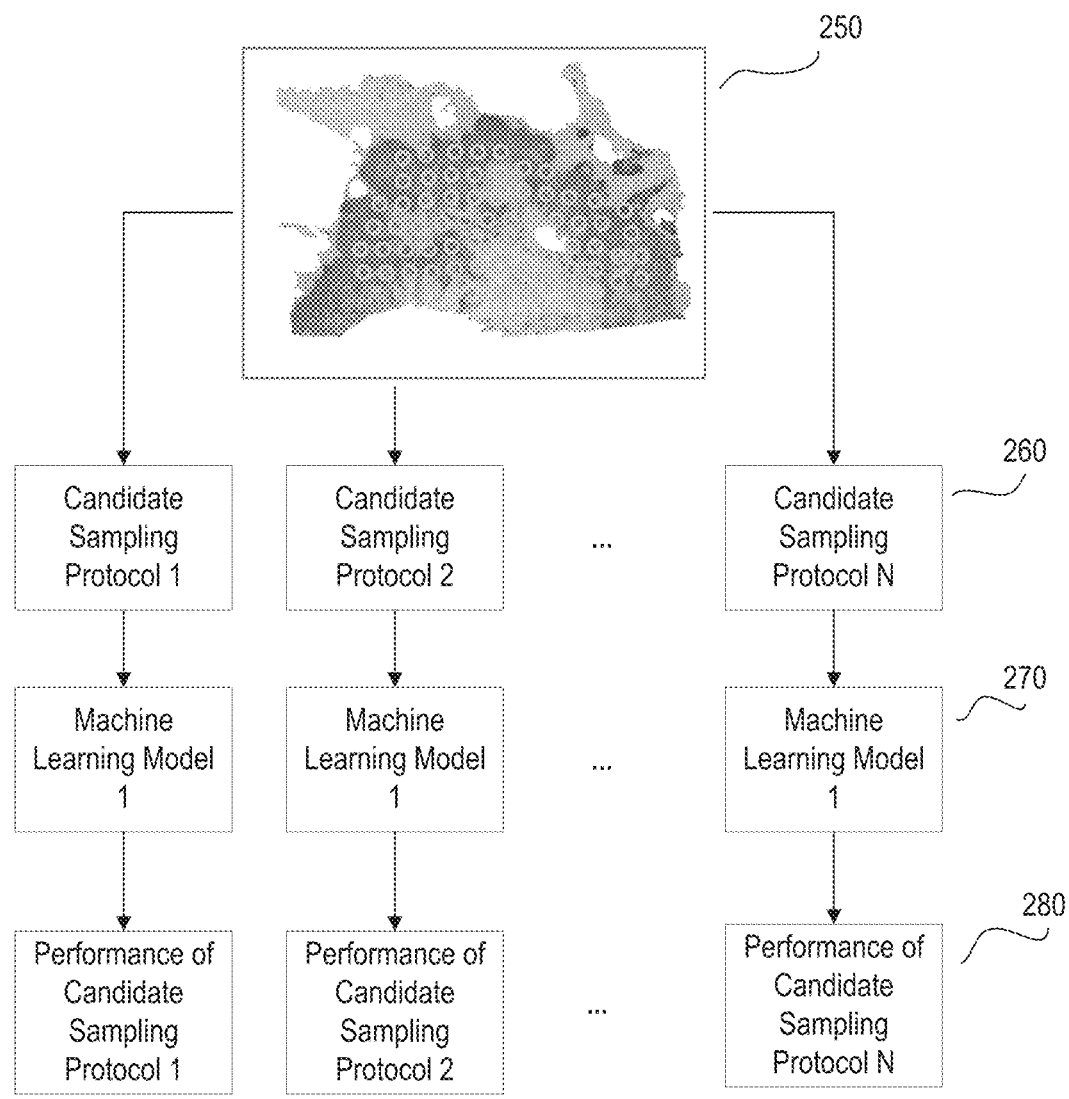
FIG. 2B illustrates a visualization of candidate sampling protocol evaluation according to some embodiments.

FIG. 2B illustrates a visualization of candidate sampling protocol evaluation according to some embodiments. At block 250, an initial plurality of cores may be selected from a WSI, for instance, using the integer linear programming approach described above with reference to FIG. 2A. While FIG. 2B illustrates a single WSI from which an initial plurality of cores was selected, it should be understood that an initial plurality of cores may be selected from a plurality of WSIs.

At block 260, from the initial plurality of cores, an exemplary system may select a first subset of tissue cores based on a first candidate sampling protocol. The first candidate sampling protocol may specify any one or more of: a first number of the tissue cores in the first subset, a first tissue core size, one or more first tissue labels corresponding to one or more regions of the tissue slide, a distance between a selected core and another core in the initial plurality, an amount of tissue contained in a core, a distance between a core from an edge of a tissue block, etc. The system may further select a second subset according to a second candidate sampling protocol, a third subset according to a third candidate sampling protocol, . . . an Nth subset according to an Nth candidate sampling protocol, and so on for any number of candidate sampling protocols. Each of the candidate sampling protocols may specify one or more different parameters from the other candidate sampling protocols.

At block 270, each of the subsets (e.g., 1, 2, . . . N) may be input into a first machine learning model (e.g., "machine learning model 1"). The machine learning model may generate a respective output based on each input subset. For instance, the machine learning model may predict patient survival, genetic mutation(s), cancer subtype(s), properties of a tumor microenvironment, and so on as described throughout.

At block 280, the system may evaluate the candidate sampling protocols (e.g., candidate sampling protocol 1, 2, . . . N) by evaluating the outputs of the machine learning model. The system may evaluate the respective outputs of the machine learning model by, for instance, comparing the outputs to one another, comparing a metric associated with each of the outputs to one another, comparing the respective outputs to a ground truth value, and/or comparing the respective outputs to an output generated by inputting a WSI (or representation thereof) into the machine learning model.

As noted above, FIG. 3 illustrates a training process for an exemplary contrastive learning algorithm, such as SimCLR, that may be used to generate embeddings based on the subsets of tissue microarray cores described herein. During training, an original image X is obtained. Data transformation or augmentation 302 can be applied to the original image X to obtain two augmented images Xi and Xj. For example, the system can randomly apply two separate data augmentation operators (e.g., crop, flip, color jitter, grayscale, blur) to obtain Xi and Xj.

Each of the two augmented images Xi and Xj is passed through an encoder to obtain respective vector representations in a latent space. In the depicted example, the two encoders have shared weights. In some examples, each encoder is implemented as a neural network. For example, an encoder can be implemented using a variant of the residual neural network ("ResNet") architecture. As shown, the two encoders output hi (vector outputted by the encoder from Xi) and hj (vector outputted by the encoder from Xj).

The two vector representations hi and hj are passed through a projection head to obtain two projections zi and zj. In some examples, the projection head comprises a series of non-linear layers (e.g., Dense-Relu-Dense layers) to apply a non-linear transformation to the vector representation to obtain the projection. The projection head amplifies the invariant features and maximizes the ability of the network to identify different transformations of the same image.

During training, the similarity between the two projections zi and zj for the same image is maximized. For example, a loss is calculated based on zi and zj, and the encoder is updated based on the loss to maximize a similarity between the two latent representations. In some examples, to maximize agreement (i.e., similarity) between the z-projections, the system can define the similarity metric as cosine similarity:

$$\text{sim}(u, v) = \frac{u^T v}{\|u\| \, \|v\|}$$

In some examples, the system trains the network by minimizing the normalized temperature-scaled cross-entropy loss:

$$\ell_{i,j} = -\log \frac{\exp(\text{sim}(z_i, z_j)/\tau)}{\sum_{k=1}^{2N} \mathbf{1}_{[k \neq i]} \exp(\text{sim}(z_i, z_k)/\tau)}$$

where $\tau$ denotes an adjustable temperature parameter. Accordingly, via training, the encoder learns to output a vector representation that preserves the invariant features of the input image while minimizing image-specific characteristics (e.g., imaging angle, resolution, artifacts).

Figure 4A:
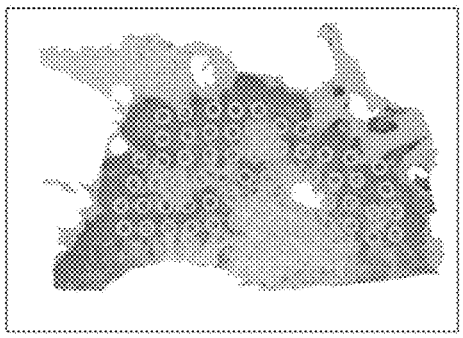
FIGS. 4A-4D illustrate exemplary tissue core placement on a whole slide image according to some embodiments.
Figure 4B:
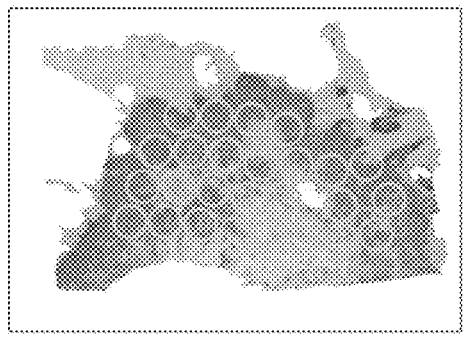
Figure 4C:
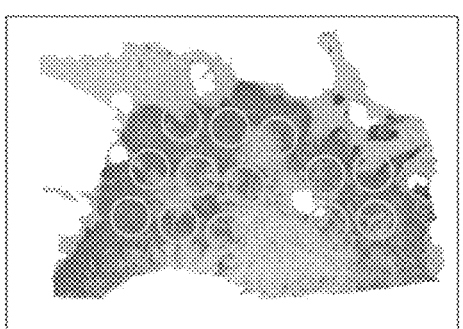
Figure 4D:
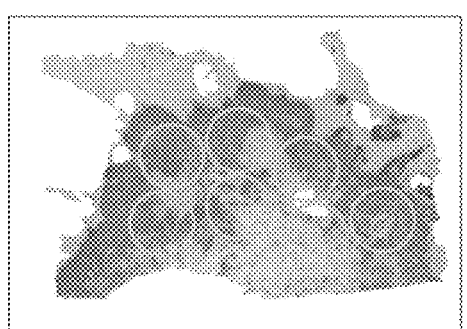

FIGS. 4A-4D respectively illustrate maximal core placements on a whole slide image (WSI) based on different core sizes where cores are constrained to be non-overlapping, avoid boundaries, and contain an approximate minimum amount of tissue. FIG. 4A illustrates an exemplary maximal placement (e.g., the initial plurality described above with reference to FIGS. 1 and 2A obtained using integer linear programming) of cores with a 0.6 mm radius. FIG. 4B illustrates an exemplary maximal placement of cores with a 1.0 mm radius. FIG. 4C illustrates an exemplary maximal placement of cores with a 1.4 mm radius. FIG. 4D illustrates an exemplary maximal placement of cores with a 2.0 mm radius. As shown, a larger core radius may result in fewer possible cores for the initial plurality of cores (e.g., because fewer cores can fit on the WSI as compared to cores of a smaller radius). However, cores of larger radius also include additional tissue which may impact downstream analyses (e.g., depending on the type of cells included in the tissue, etc.). For instance, larger tissue cores may include regions of tissue that include cancerous cells, healthy cells, and necrotic cells, while a smaller tissue core may only include cancer cells. In some embodiments, however, a smaller tissue core may include just as many different types of cells as a larger tissue core. As discussed below with reference to an exemplary sampling study performed using a publicly available dataset of whole slide images, machine learning models performed some predictive tasks better using smaller core sizes than larger core sizes, and vice versa. Thus, the optimal tissue core size may depend on the downstream machine learning task to which it is applied.

Figure 5:
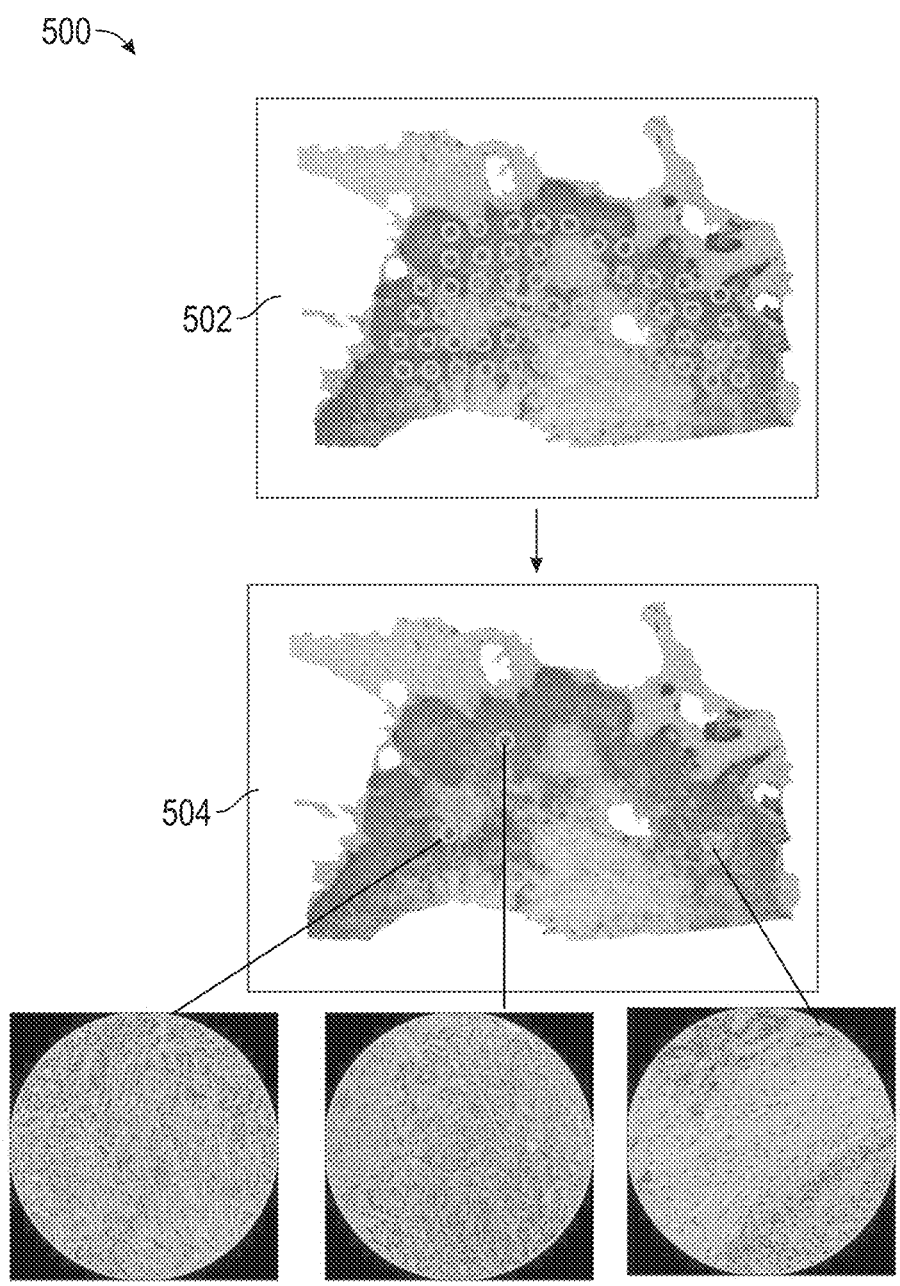
FIG. 5 illustrates an exemplary tissue core placement on a whole slide image and a subset of cores selected from the tissue core placement according to some embodiments.

FIG. 5 illustrates an exemplary initial plurality of cores 502 obtained from a WSI and a subset of tissue microarray cores 504 selected from the initial plurality. The initial plurality may be obtained using integer linear programming to determine the maximum number of cores that can be obtained from the WSI based on a set of constraints, for instance, as described above with reference to FIGS. 1 and 2A and described in further detail below with reference to an exemplary study conducted using a publicly available dataset of whole slide images. The subset of tissue cores 504 may be selected based on a candidate sampling protocol, for instance, the first, second, third, etc. sampling protocols described above with reference to FIG. 1. As described above, the candidate sampling protocol may specify any one or more of: a number of the tissue cores in the first subset, a tissue core size, one or more tissue labels corresponding to one or more regions of the tissue slide, a distance between a selected core and another core in the initial plurality and/or another core in the subset, an amount of tissue contained in a core, a distance between a core from an edge of a tissue block, etc. The subset of tissue microarray cores 502 may include one or more tissue cores that include tissue assigned the same label (e.g., by a segmentation model as described above), one or more cores that are the same size, one or more cores that have the same approximate amount of tissue, etc. As described throughout, in some embodiments, the subset of tissue microarray core images may be input into a downstream machine learning model as embeddings, and an output of the machine learning model may be evaluated by comparing it to a ground truth value, an output generated based on one or more embeddings representing a different subset (e.g., selected from the same initial plurality or a different initial plurality obtained from a different whole slide image) of tissue microarray core images, and/or an output generated based on one or more embeddings representing a whole slide image. In some embodiments, the one or more embeddings representing the subset may be input into a plurality of different machine learning models.

The exemplary systems and methods described herein were tested in an experimental study that evaluated various machine learning model outputs based on subsets of tissue microarray cores images obtained using a variety of different sampling protocols. The study, set forth in detail below, provides additional information regarding exemplary mathematical equations that may be applicable to perform various steps of the process 100 described above (e.g., using integer linear programming to obtain an initial plurality of tissue microarray cores from a whole slide image, selection of one or more subsets from the initial plurality, embedding generation, etc.).

Exemplary Core Selection Study

An experimental implementation study of the systems and method described herein for evaluating sampling protocols (e.g., process 100 described above with reference to FIG. 1) was carried out on a publicly available dataset, The Cancer Genome Atlas breast carcinoma (BRCA) cohort, of WSIs obtained from real patients. Downstream performance was evaluated for overall survival prediction, BRCA immunohistochemistry (IHC) subtype prediction, and mutation status prediction in 3 genes frequently mutated in BRCA: TP52, PIK3CA, and CDH1. The experiment further analyzed the tradeoffs between increasing contextual information provided by more, larger cores and the decreasing experimental cost of fewer, smaller cores. In the latter case, samples from more patients can fit on the same plate, which can be preferable in a scenario where a limited budget is available for tissue microarray (TMA) data generation. As described throughout, the in silico TMA optimization protocol may be divided into three main steps: core placement, core sampling, and core evaluation. Core placement may include identifying a maximum number of cores that can be obtained from a WSI based on a set of constraints. Core sampling includes selecting one or more subsets of the initial plurality of cores. Evaluation involves evaluating machine learning model outputs based on input subsets of cores.

As noted, the study utilized a dataset of real patient WSIs, where each patient has one or more whole tissue section (WTS) slides $\{x_1, \ldots, x_s\}$, and a specified set of N TMA sampling protocols $P=\{(r_1, f_1), \ldots, (r_N, f_N)\}$, where r indicates the desired core radius and f indicates the number of cores that should be sampled from each WSI. N corresponding TMA datasets were synthesized, sampling f radius-r cores from each patient slide $x_i$. In order to mimic realistic TMA datasets, several additional constraints were imposed on the sampled cores. For instance, the constraints included that cores taken from the same slide must be separated by a predefined distance (e.g., at least 0.2 millimeters (mm)); second, cores must be at least a predefined distance (e.g., 2.0 mm) from the specimen edge; finally, at least a predefined amount (e.g., 85%) of the core must contain tissue. If fewer than f cores could be sampled from a slide given the constraints, the maximum possible number of cores was taken. Next, the performance of each synthetic TMA dataset was evaluated for predicting overall survival, IHC subtype, and mutation status.

Detailed Implementation

At step 1, an initial plurality of cores were obtained in silico using integer linear programming (e.g., as described above with reference to FIG. 1 and FIG. 2A). Obtaining the initial plurality included identifying the possible cores C from a given slide x. To avoid repeated computation between multiple TMA sampling protocols with the same core radius r, the core placement was determined in a WSI that would maximize the number of possible cores given the realistic TMA constraints, for instance, as shown above in FIGS. 4A-4F, which provides exemplary illustrations of maximal core packing using an integer linear programming approach based on different constraints. For the WSI depicted in FIG. 4E, 34 0.6 mm radius cores were possible, which decreased to 7 when the radius was increased to 1.4 mm, as shown in FIG. 4F. Cores were constrained to be non-overlapping, avoid tissue edges, and contain at least 85% tissue.

More generally, given a WSI $x \in [0, 1]^{W \times H \times 3}$, a binary foreground segmentation $m \in \{0, 1\}^{W \times H}$ is computed with a frequency masking strategy, where 1 indicates that the pixel contains a predefined amount of tissue (e.g., at least 85%) and where W refers to a width of the WSI and H refers to a height of the WSI. The problem is then relaxed to a gridded space to reduce the number of variables and improve efficiency. Given the WSI microns per pixel (mpp) resolution, a new grid unit $\Delta$ can be computed that evenly divides the original resolution, desired core radius, and minimum distances between cores and from a core to the tissue edge. Mean pooling is applied over neighboring pixels in the foreground mask to estimate the average tissue content in each gridded unit as $\overline{m} \in [0, 1]^{W_\Delta \times H_\Delta}$. In the gridded $W_\Delta \times H_\Delta$-dimensional space, the core packing problem can be solved using a placement variable $a \in \{0, 1\}^{W_\Delta \times H_\Delta}$, where $a[i, j]=1$ means that a core should be placed in the $2r \times 2r$ mm² area anchored at the top-left coordinate (i, j).

In the exemplary study, the first TMA constraint required that cores be non-overlapping and contain at least 0.2 mm between adjacent cores. Let $r_\Delta = (r \times 10^3)/\Delta$ and $p_\Delta = 200/\Delta$ be the core radius and minimum distance between cores in the gridded space. For all pixels i, j and corresponding submatrices of assignment variables, the constraint $\Sigma a[i:i+2r_\Delta+p_\Delta, j:j+2r_\Delta+p_\Delta] \leq 1$, where the sum is over all entries in the sub-matrix. Taken over $\forall i, j$, this yields $W_\Delta \times H_\Delta$ constraints.

The second constraint required that cores contain sufficient foreground tissue. To enforce this during the exemplary implementation, a hard constraint was included that $a[i, j]=0$ for all anchor points (i, j) in the gridded pixel space with $$\left(\frac{1}{(2r_\Delta)^2}\right) \overline{m}[i:i+2r_\Delta, j:j+2r_\Delta] < 0.9,$$

which guarantees the 85% minimum foreground core threshold. This step may be repeated to avoid cores being taken too close to the tissue edge with $e_\Delta=(2\times10^3)/\Delta$ being the minimum distance from the tissue edge for each core in the gridded units. Specifically, a hard constraint of $[i,j]=0$ for all $(i, j)$ with $$\left(\frac{1}{(2r_\Delta+e_\Delta)^2}\right)m\bigl[i-e_\Delta:i+2r_\Delta+e_\Delta,\ j-e_\Delta:j+2r_\Delta+e_\Delta\bigr]<0.9,$$

where 90% foreground in the surrounding region is taken to indicate that the core is not too close to the tissue edge.

An edge case in which a tissue block extends all the way to an edge of a slide may be handled by introducing a slide edge constraint. Specifically, $\Sigma_{i,j\in sl_{edge}}a[i,j]=0$, where $sl_{edge}$ is the set of all anchor indices that would locate a core less than $e_\Delta$ units from the edge of the slide image.

The maximal core packing problem (e.g., determining the maximum number of cores that can be obtained from a whole slide image) can be solved as:

$$\hat{a}=\max_{a\in\{0,1\}^{W_\Delta\times H_\Delta}}\sum_{i=1}^{W_\Delta}\sum_{j=1}^{H_\Delta}a[i,j] \quad (1)$$

subject to the non-overlapping core constraints, the minimum core foreground and surrounding core foreground constraints, and the minimum distance from slide edge constraints. One skilled in the art would understand that a* as used above with reference to FIG. 2 may refer to the same solution to the core maximal core packing problem as a. This maximization problem over a binary variable with four constraint types is well suited to an integer linear programming (ILP) solution. In some embodiments, an ILP solver such as cvxpy may be used to compute the optimal core placement $\hat{a}(r)$ that defines the location of radius-r cores $\hat{C}(r, x)$ in x such that no additional core can be added without violating a constraint. In some embodiments, a mixed integer linear programming (ILP) technique may be used.

At step 2, after determining the maximal possible number of cores for a given slide, a plurality of synthetic TMA datasets were produced for each slide using different sampling protocols (e.g., as described above with reference to FIG. 1 and FIGS. 2A-2B). For a given protocol (r,f), one or more subsets off cores are taken from the set $\hat{C}(r, x)$ as the TMAs produced from slide x. If $\hat{C}(r, x)<f$, then the entire valid core set is obtained. This process may be repeated for each slide in the WSI dataset to produce synthetic TMA datasets.

As described above, the study utilized a dataset of real patient WSIs, where each patient has one or more WTS slides $\{x1, \ldots, xs\}$, and a specified set of N TMA sampling protocols $P=\{(r_1, f_1), \ldots, (r_N, f_N)\}$, where r indicates the desired core radius and f indicates the number of cores that should be sampled from each WSI. N corresponding TMA datasets were synthesized, sampling f radius-r cores from each patient slide $x_1$. For instance, if there are 10 sampling protocols P, then 10 subsets of cores may be selected from a patient slide based on a respective protocol. 10 TMA datasets may be obtained by sampling 10 subsets from each patient slide in the WSI dataset, which may be used to evaluate downstream machine learning model performance for each sampling protocol P.

Accordingly, at step 3, after obtaining the in silico TMA datasets, the TMA datasets were evaluated on three downstream tasks, predicting: overall survival (OS), IHC subtype, and mutation status (e.g., as described above with reference to FIGS. 1 and 2). As described throughout, additional downstream tasks are within the scope of this disclosure, but this study focused on the aforementioned three tasks. For downstream tasks, when a patient had 2 or more slides, the predictions were averaged across samples taken from each of the slides. OS predictions were evaluated using the inverse probability of censoring weighted concordance statistic (C-statistic), IHC subtype and mutation status predictions were evaluated using the classification accuracy. Prior to inputting cores into the machine learning models to predict OS, IHC subtype, and mutation status, the TMA cores were embedded using a hierarchical image pyramid transformer (HIPT) model with a base vision transformer to produce patch-level representations, which are designed to perform well on a variety of downstream tasks. HIPT was used to tile each core into $256^2$ image patches at 0.5 mpp resolution and produces a 768-dimensional embedding for each patch.

For each input WSI x, the output of the HIPT embedding module for sampling protocol (r, f) is a set of embeddings $z\in\mathbb{R}^{f'\times p\times 768}$, where $f'\le f$ is the number of cores taken from slide x and p is the number of $256^2$ patches that make up each core. Multi-head attention pooling was used to produce a single embedding per slide, with attention scores:

$$\alpha^{(h)}=\sigma(\text{MLP}(z))\in[0,1]^{f'\times p\times 1} \quad (2)$$

for each head $h\in\{1, 2, 3\}$, with $\sigma()$ the softmax function and MLP a two-layer multi-layer perceptron (MLP) network. The scores were used to take the convex combination of embeddings belonging to cores from the same slide as $$\bar{z}^{(h)}=\sum_{\varsigma=1}^{f'}\sum_{\psi=1}^{p}\alpha^{(h)}[\varsigma,\psi](z[\varsigma,\psi])\in\mathbb{R}^{768}. \quad (3)$$

Finally, concatenation was performed over each head to produce a final embedding $z_{i,j}\in\mathbb{R}^{2304}$ (2304=3×768) for patient i and slide j. The scoring module may be trained in conjunction with the downstream task.

Each patient i in the WSI dataset had associated metadata, including OS data for death time and censoring status; IHC subtype, where BRCA patients re classified according to hormone receptor status with positive and negative designations for each of: human epidermal growth factor receptor 2 (HER2), estrogen receptor (ER), and progesterone receptor (PR); and mutation status in common genes that impact tumor development and treatment in BRCA: TP53, PIK3CA, and CDH1.

For OS prediction, a two-layer MLP with Cox partial log-likelihood loss was trained to predict the risk score of patient i based on data from slide j. The risk score that the two-layer MLP with Cox partial log-likelihood loss was trained to predict can be represented as $\rho_{i,j}=g_{OS}(z_{i,j})\in\mathbb{R}$.

Binary cross entropy was used to learn IHC status and mutation status. During training, cases were upsampled from underrepresented classes to approximately balance the training dataset labels. In the IHC status experiment, some patients only had labels for a subset of IHC receptors; all patients with at least one receptor status were included, and any unknown receptor label(s) were masked when computing loss.

As noted above, the Cancer Genome Atlas (TCGA) BRCA cohort of WSIs were used in the experimental study described herein. 5-fold cross validation was conducted wherein 20% of the non-test data was used for validation.

Training, validation, and test sets were split by patient, and were repeated in each experiment with 5 different random seeds to minimize the impact of model initialization and test splits. Different TMA sampling protocols used the same random seeds. All models were trained with the Adam optimizer for a maximum of 200 epochs and early stopping with a validation loss patience of 20. For the IHC and mutation prediction models the learning rate was varied from [1e-4, 1e-3] with a 20 epoch ramp-up; for the OS risk prediction model a cosine decay schedule between 1e-5 and 1e-4 was used with 10 epoch ramp-up, 10 epoch period, and maximum of three resets.

Results

For each experimental core size, a model was also trained based on the WSIs for all slides that contained at least one core to control for the number of slides that could be captured with different core sizes. In total, the dataset of 0.6 mm cores represented 921 slides from 807 patients; the 1.0 mm dataset 792 slides from 734 patients; the 1.4 mm dataset 697 slides from 662 patients; and the 2.0 mm dataset 555 slides from 533 patients.

Figure 6A:
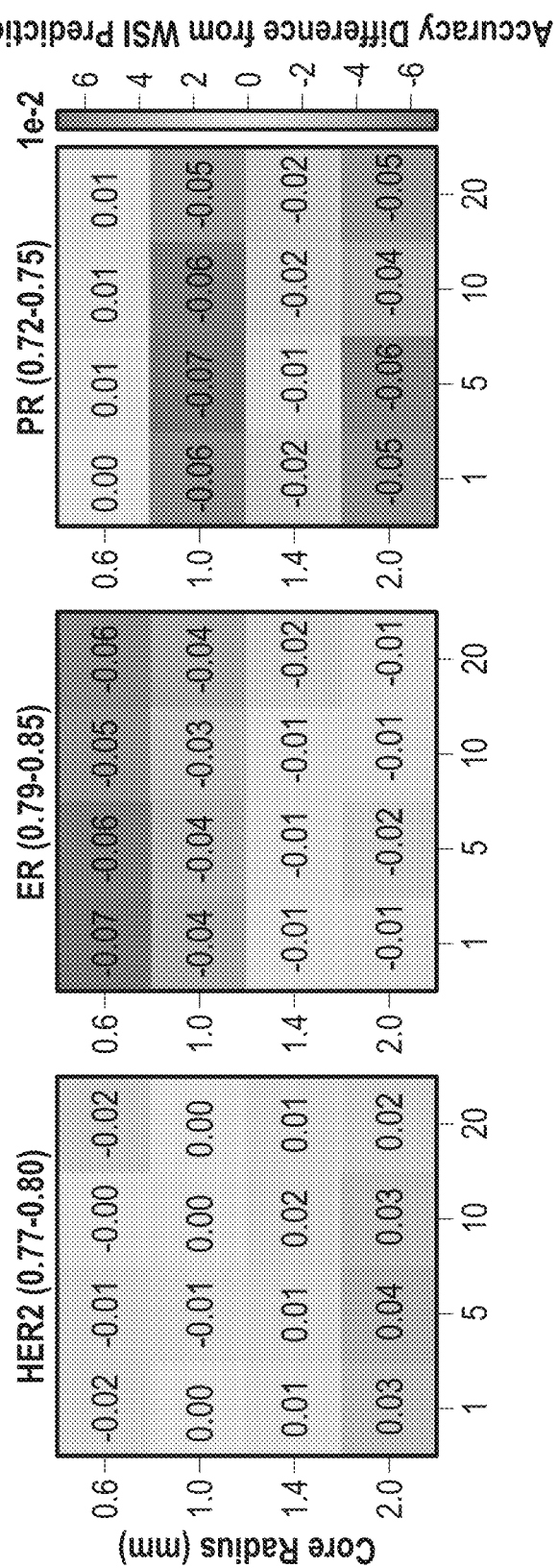
FIGS. 6A-6D illustrate results of machine learning model evaluations based on different tissue core sampling protocols according to some embodiments.
Figure 6B:
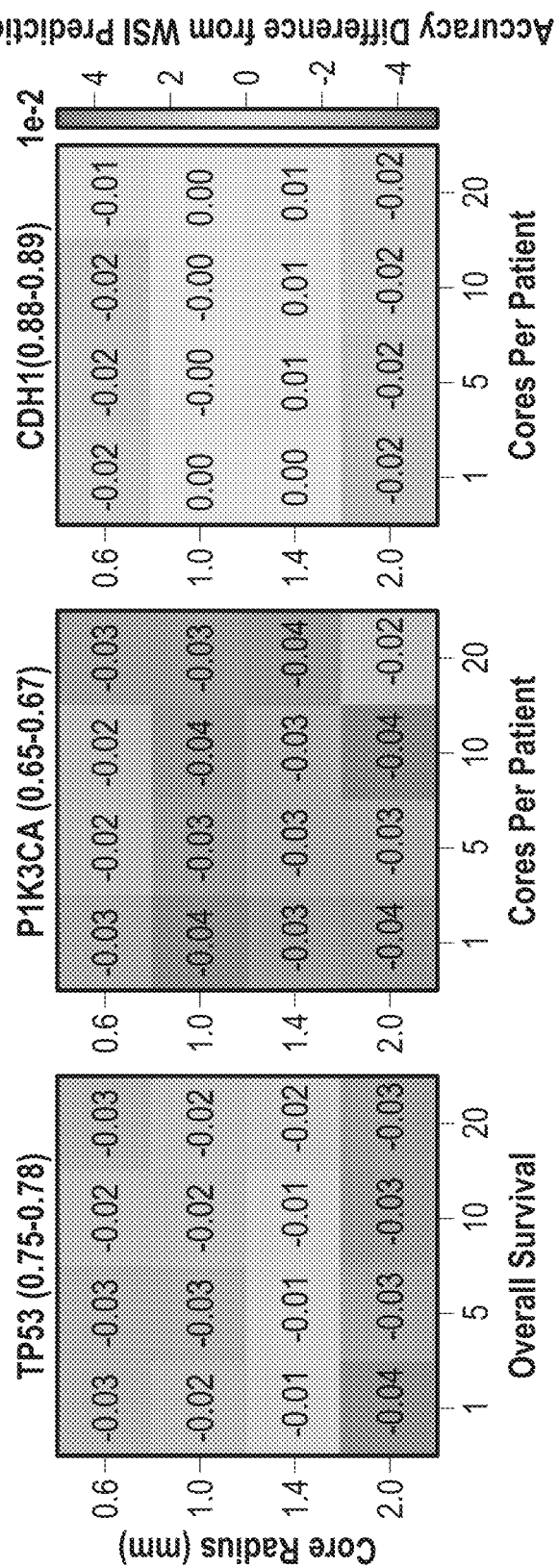
Figure 6C:
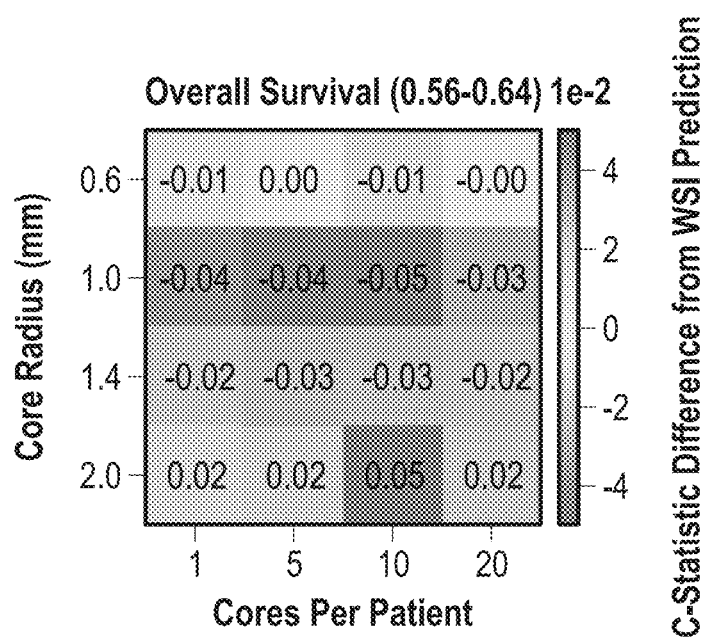
Figure 6D:
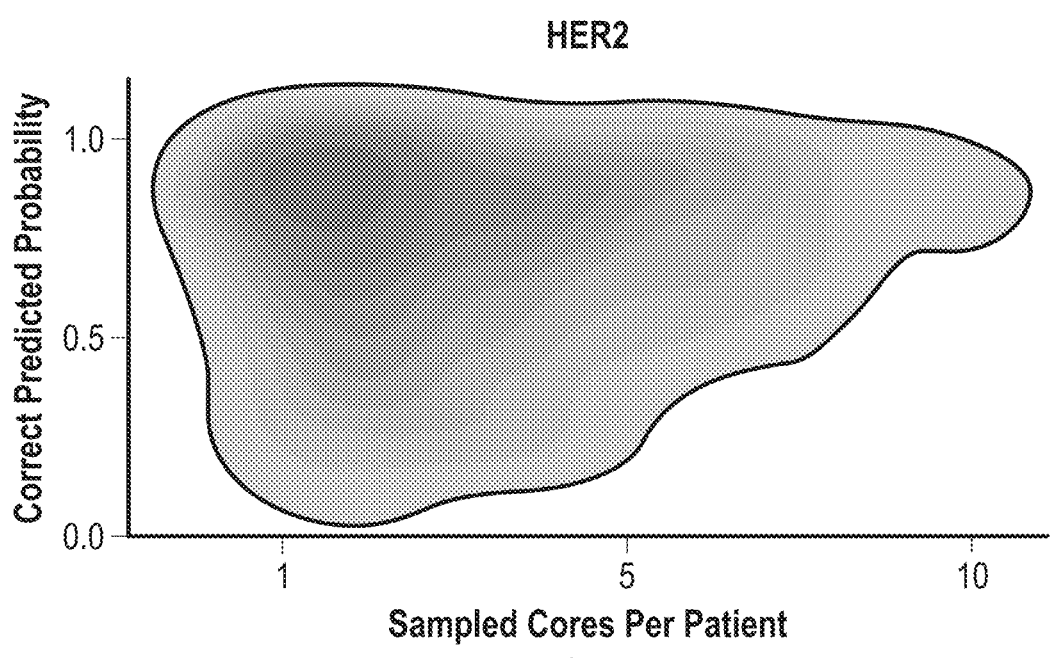

Results indicated that the optimal TMA sampling procedure varied by machine learning task; although, the 1.4 mm radius cores were the best choice on average, as illustrated in FIGS. 6A-6C, which depict the performance of different tissue microarray (TMA) sampling protocols for predicting IHC subtype, mutation status, and patient survival. Specifically, FIGS. 6A-6C, depict heatmaps of the mean accuracy (shown in FIGS. 6A and 6B) in the IHC (FIG. 6A) and mutation (FIG. 6B) prediction tasks, and the mean C-statistic (shown in FIG. 6C) in the OS (FIG. 6C) prediction task, subtracted by the average whole slide image (WSI) dataset performance for the same core size. Each row and column in the heatmap corresponds to a different core size and different number of sampled cores per slide respectively. Redder colors (as shown in the color figures filed in U.S. Provisional Application 63/548,140, which is incorporated herein by reference and which this application claims priority to) correspond to protocols with better performance. FIG. 6D illustrates a density plot showing the predicted probability of the correct HER2 status for each patient compared to the number of actually sampled for that patient.

Larger cores, with 1.4 mm and 2.0 mm radii had the highest HER2 and ER IHC status prediction accuracy, while PR status prediction performed best with 0.6 mm cores. Further, 1.0 mm and 1.4 mm cores had highest accuracy for CDH1 mutation status prediction. All TMA cores underperformed on TP53 and PIK3CA mutation prediction relative to the WSI datasets, but achieved competitive performance on CDH1 status prediction. Notably, the largest TMA core size had the highest C-statistic in OS prediction, reflecting the value of large tissue contexts that contain mainly foreground tissue in this task. This may reflect the impact that abundance of rare cell types, such as Tumor Infiltrating Lymphocytes (TILs), has on OS prediction.

Additionally, the number of cores sampled per patient had relatively low impact on the downstream task's performance in the experimental averages (FIG. 6A-6C). This may be related to the low number of valid cores in many slides. In a case study with 0.6 mm radius cores, HER2 status prediction accuracy and the number of cores sampled for each patient was examined, where the maximum number of cores was set to 10. Findings indicated that patients with more sampled cores had higher average accuracy (as shown in FIG. 6D), though the dataset average was dominated by patients with fewer possible cores per slide.

Second Exemplary Study

A second case study was conducted on HER2 status prediction to test the TMA sampling protocol optimization pipeline in a limited budget setting, reflecting the real-world value of TMAs. The trial budget permitted 3 tissue plate stains for each model training and validation data, with 20% validation cores. Each 75×26 $mm^2$ plate contains a maximum of 279×0.6 mm cores, 138×1.0 mm cores, 90×1.4 mm cores, or 52×4.0 mm cores, allowing for 3 mm from the plate edge and 1 mm between core spots. The HER2 status prediction model was trained and evaluated 5 times over 5 different test sets, where the test patients were shared for all TMA sampling procedures.

The in silico TMA protocol evaluation was able to capture the tradeoff between dataset staining cost and the data-hungry ML-model performance, and suggested a TMA sampling procedure designed for the specific task and budgetary constraints. Results indicated that the 1.0 mm cores with a maximum of 10 cores per WSI performed best on the HER2 subtyping task, with a mean accuracy of 0.80 and standard deviation of 0.04, relative to a mean accuracy of 0.72 with a standard deviation of 0.09 for a comparable training dataset with 3 WSIs. This experimental sampling protocol was also among the best-performing methods for even more limited budgets allowing for 1 or 2 slides.

Figure 7:
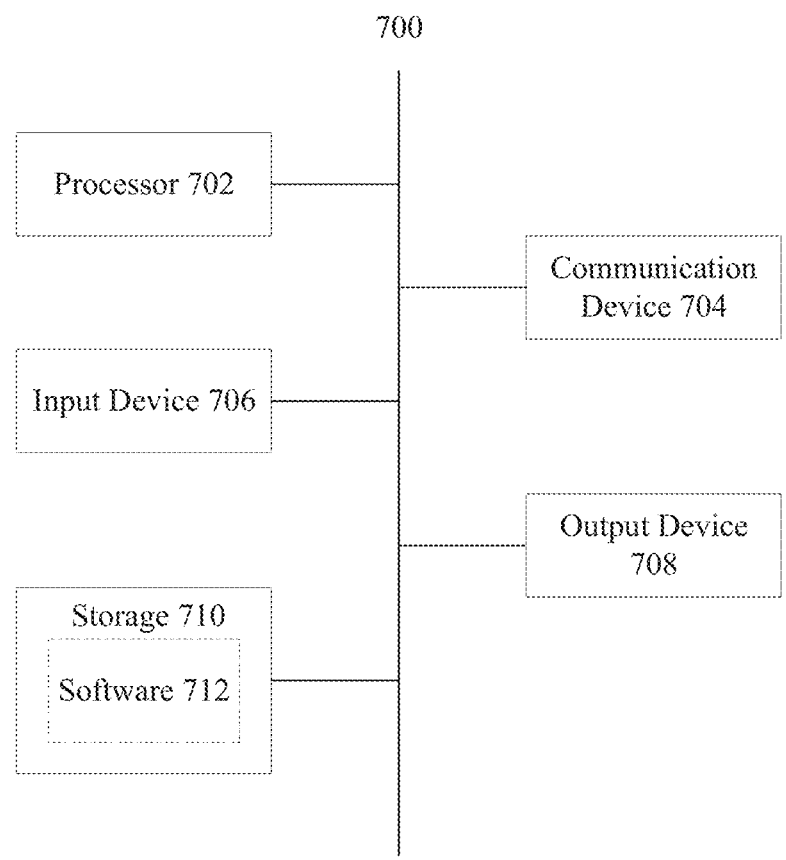
FIG. 7 illustrates an exemplary computing system according to some embodiments.

FIG. 7 depicts an exemplary computing device 700, in accordance with one or more examples of the disclosure. Device 700 can be a host computer connected to a network. Device 700 can be a client computer or a server. As shown in FIG. 6, device 700 can be any suitable type of microprocessor-based device, such as a personal computer, workstation, server, or handheld computing device (portable electronic device) such as a phone or tablet. The device can include, for example, one or more of processors 702, input device 706, output device 708, storage 710, and communication device 704. Input device 706 and output device 708 can generally correspond to those described above and can either be connectable or integrated with the computer.

Input device 706 can be any suitable device that provides input, such as a touch screen, keyboard or keypad, mouse, or voice-recognition device. Output device 708 can be any suitable device that provides output, such as a touch screen, haptics device, or speaker.

Storage 710 can be any suitable device that provides storage, such as an electrical, magnetic, or optical memory, including a RAM, cache, hard drive, or removable storage disk. Communication device 704 can include any suitable device capable of transmitting and receiving signals over a network, such as a network interface chip or device. The components of the computer can be connected in any suitable manner, such as via a physical bus or wirelessly.

Software 712, which can be stored in storage 710 and executed by processor 702, can include, for example, the programming that embodies the functionality of the present disclosure (e.g., as embodied in the devices as described above).

Software 712 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 710, that can contain or store programming for use by or in connection with an instruction execution system, apparatus, or device.

Software 712 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Device 700 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 700 can implement any operating system suitable for operating on the network. Software 712 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A system for determining a sampling protocol for sampling tissue cores for a tissue microarray, the system comprising one or more processors, memory, and one or more programs stored in the memory for execution by the one or more processors, the one or more programs including instructions that when executed by the one or more processors cause the system to:
receive an initial plurality of tissue cores from an image of a tissue slide;
select a first subset of the initial plurality of tissue cores based on a first candidate sampling protocol;
input the first subset of the plurality of tissue cores into a machine learning model;
evaluate the first candidate sampling protocol by evaluating a first output of the machine learning model based on the first subset of the plurality of tissue cores;
select a second subset of the initial plurality of tissue cores based on a second candidate sampling protocol;
input the second subset of the plurality of tissue cores into the machine learning model;
evaluate the second candidate sampling protocol by evaluating a second output of the machine learning model based on the second subset of the plurality of tissue cores; and
determine the sampling protocol based on the evaluation of the first candidate sampling protocol and the second candidate sampling protocol.

2. The system of claim 1, wherein the one or more programs include instructions that when executed by the one or more processors cause the system to:
select a third subset of the initial plurality of tissue cores based on a third candidate sampling protocol;
input the third subset of the plurality of tissue cores into the machine learning model;
evaluate the third candidate sampling protocol by evaluating a third output of the machine learning model based on the third subset of the plurality of tissue cores; and
wherein the determination of the sampling protocol is further based on the evaluation of the third candidate sampling protocol.

3. The system of claim 2, wherein the first output, the second output, and the third output comprise a disease diagnosis, a probability of survival, a disease subtype, a genetic sequence, a rare variant association, or any combination thereof.

4. The system of claim 1, wherein evaluating the first output of the machine learning model comprises: comparing the first output of the machine learning model to a ground truth value; and wherein evaluating the second output of the machine learning model comprises comparing the second output to at least one of the ground truth value and the first output.

5. The system of claim 1, wherein the first candidate sampling protocol specifies any one or more of: a first number of the tissue cores in the first subset, a first tissue core size, a first amount of tissue in each core of the first subset, a first minimum distance between each tissue core of the first subset and an edge of a tissue, and one or more first tissue labels corresponding to one or more regions of the tissue slide.

6. The system of claim 5, wherein generating the second candidate sampling protocol comprises any of: modifying the first number of the tissue cores, modifying the first tissue core size, modifying the first amount of tissue in each core, modifying the first minimum distance between each tissue core of the first subset and the edge of the tissue edge, and modifying the one or more first tissue labels.

7. The system of claim 5, wherein the one or more first tissue labels corresponding to the one or more regions of the tissue slide are associated with a diseased tissue or a healthy tissue.

8. The system of claim 5, wherein the one or more first tissue labels corresponding to the one or more regions of the tissue slide are associated with any of: an invasive carcinoma; a carcinoma in situ, a tumor invasive front, necrotic tissue, or a healthy tissue.

9. The system of claim 5, wherein the one or more first tissue labels are based on one or more tissue labels assigned to the or more regions of the image by providing the image to an image segmentation model.

10. The system of claim 9, wherein the image segmentation model is trained based on labeled tissue slide images.

11. The system of claim 9, wherein a respective tissue label of the one or more first tissue labels is assigned to a pixel of the image.

12. The system of claim 1, wherein the initial plurality of tissue cores is obtained using integer linear programming by maximizing an objective function based on a set of constraint parameters.

13. The system of claim 12, wherein the set of constraint parameters comprises a tissue core size, a minimum distance between two tissue cores, a minimum tissue content, a minimum distance between a tissue core and an edge of a tissue edge, or any combination thereof.

14. The system of claim 12, wherein the initial plurality of tissue cores comprises a number of tissue cores that can be obtained from the tissue slide based on the set of constraint parameters.

15. The system of claim 1, wherein the machine learning model comprises a trained classifier model or a trained regression model.

16. The system of claim 1, wherein the tissue slide comprises any of: cancerous tissue, tumor-adjacent normal tissue, necrotic tissue, and randomly sampled tissue.

17. The system of claim 1, wherein inputting the first subset into the machine learning model comprises:
   generating at least one embedding based on each tissue core of the first subset of the initial plurality of tissue cores; and
   inputting the at least one embedding into the machine learning model.

18. A method for determining a sampling protocol for sampling tissue cores for a tissue microarray, the method comprising:
   receiving an initial plurality of tissue cores from an image of a tissue slide;
   selecting a first subset of the initial plurality of tissue cores based on a first candidate sampling protocol;
   inputting the first subset of the plurality of tissue cores into a machine learning model;
   evaluating the first candidate sampling protocol by evaluating a first output of the machine learning model based on the first subset of the plurality of tissue cores;
   selecting a second subset of the initial plurality of tissue cores based on a second candidate sampling protocol;
   inputting the second subset of the plurality of tissue cores into the machine learning model;
   evaluating the second candidate sampling protocol by evaluating a second output of the machine learning model based on the second subset of the plurality of tissue cores; and
   determining the sampling protocol based on the evaluation of the first candidate sampling protocol and the second candidate sampling protocol.

19. The method of claim 18, wherein the one or more programs include instructions that when executed by the one or more processors cause the system to:
   select a third subset of the initial plurality of tissue cores based on a third candidate sampling protocol;
   input the third subset of the plurality of tissue cores into the machine learning model;
   evaluate the third candidate sampling protocol by evaluating a third output of the machine learning model based on the third subset of the plurality of tissue cores; and
   wherein the determination of the sampling protocol is further based on the evaluation of the third candidate sampling protocol.

20. The method of claim 19, wherein the first output, the second output, and the third output comprise a disease diagnosis, a probability of survival, a disease subtype, a genetic sequence, a rare variant association, or any combination thereof.

21. The method of claim 18, wherein evaluating the first output of the machine learning model comprises: comparing the first output of the machine learning model to a ground truth value; and wherein evaluating the second output of the machine learning model comprises comparing the second output to at least one of the ground truth value and the first output.

22. The method of claim 18, wherein the first candidate sampling protocol specifies any one or more of: a first number of the tissue cores in the first subset, a first tissue core size, a first amount of tissue in each core of the first subset, a first minimum distance between each tissue core of the first subset and an edge of a tissue, and one or more first tissue labels corresponding to one or more regions of the tissue slide.

23. The method of claim 22, wherein generating the second candidate sampling protocol comprises any of: modifying the first number of the tissue cores, modifying the first tissue core size, modifying the first amount of tissue in each core, modifying the first minimum distance between each tissue core of the first subset and the edge of the tissue edge, and modifying the one or more first tissue labels.

24. The method of claim 22, wherein the one or more first tissue labels are based on one or more tissue labels assigned to the or more regions of the image by providing the image to an image segmentation model.

25. The method of claim 18, wherein the initial plurality of tissue cores is obtained using integer linear programming by maximizing an objective function based on a set of constraint parameters.

26. The method of claim 25, wherein the set of constraint parameters comprises a tissue core size, a minimum distance between two tissue cores, a minimum tissue content, a minimum distance between a tissue core and an edge of a tissue edge, or any combination thereof.

27. The method of claim 25, wherein the initial plurality of tissue cores comprises a number of tissue cores that can be obtained from the tissue slide based on the set of constraint parameters.

28. The method of claim 18, wherein inputting the first subset into the machine learning model comprises:
   generating at least one embedding based on each tissue core of the first subset of the initial plurality of tissue cores; and
   inputting the at least one embedding into the machine learning model.

29. A non-transitory computer-readable medium storing instructions for determining a sampling protocol for sampling tissue cores for a tissue microarray, wherein the instructions are executable by a system comprising one or more processors to cause the system to:
   receive an initial plurality of tissue cores from an image of a tissue slide;
   select a first subset of the initial plurality of tissue cores based on a first candidate sampling protocol;
   input the first subset of the plurality of tissue cores into a machine learning model;
      evaluate the first candidate sampling protocol by evaluating a first output of the machine learning model based on the first subset of the plurality of tissue cores;
   select a second subset of the initial plurality of tissue cores based on a second candidate sampling protocol;
   input the second subset of the plurality of tissue cores into the machine learning model;
   evaluate the second candidate sampling protocol by evaluating a second output of the machine learning model based on the second subset of the plurality of tissue cores; and determine the sampling protocol based on the evaluation
of the first candidate sampling protocol and the second
candidate sampling protocol.

\* \* \* \* \*